United States Patent [19]
Welch et al.

[11] Patent Number: 5,779,964
[45] Date of Patent: Jul. 14, 1998

[54] METHOD OF MAKING A MALE CATHETER

[75] Inventors: Daniel P. Welch, Zimmerman; Thomas D. Ryan, Minnetonka; Erik M. Knutson, Minneapolis, all of Minn.

[73] Assignee: Mentor Corporation, Santa Barbara, Calif.

[21] Appl. No.: 122,399

[22] Filed: Sep. 17, 1993

Related U.S. Application Data

[63] Continuation of Ser. No. 754,054, Sep. 3, 1991, abandoned.

[51] Int. Cl.⁶ .......................... B29C 41/08; B29C 41/14
[52] U.S. Cl. .......................... 264/255; 264/301; 264/304; 264/305; 264/306; 264/308
[58] Field of Search .......................... 264/301, 255, 264/308, 303, 215, 304, 305, 306; 425/269, 275

[56] References Cited

U.S. PATENT DOCUMENTS

| | | | |
|---|---|---|---|
| 2,337,116 | 12/1943 | Limbert et al. | 264/303 |
| 2,371,883 | 11/1945 | Gammeter et al. | 264/303 |
| 2,726,924 | 12/1955 | Rumbold | 264/303 |
| 4,340,348 | 7/1982 | Kurtz | 425/270 |
| 4,390,492 | 6/1983 | Kurtz | 264/255 |
| 4,464,796 | 8/1984 | Heissenberger et al. | 425/275 |
| 4,638,790 | 1/1987 | Conway et al. | 604/352 |
| 4,863,449 | 9/1989 | Therriault et al. | 604/352 |
| 5,304,337 | 4/1994 | Chen et al. | 425/275 |
| 5,314,654 | 5/1994 | Harlambopoulos | 264/301 |

*Primary Examiner*—Angela Y. Ortiz
*Attorney, Agent, or Firm*—Larkin, Hoffman, Daly & Lindgren, Ltd.

[57] ABSTRACT

A male urinary catheter and method of making same. The catheter employs a condom like sheath of silicone rubber which sealingly engages the penis of the patient. A catheter stem at the distal end of the sheath couples to a urine collection system. The sheath is sealed to the penis by an adhesive which is applied to the outer surface of the sheath at the time of manufacture. A surface preparation layer is applied over the adhesive. The sheath is rolled up from the proximal end. The sheath is unrolled to apply it to the patient. During the unrolling process, the adhesive layer is removed from the outer surface and deposited on the inner surface of the sheath.

6 Claims, 4 Drawing Sheets

METHOD OF MAKING A MALE CATHETER

This patent application is a continuation of U.S. Ser. No. 07/754,054, filed Sep. 3, 1991, now abandoned, entitled "Male Catheter and Method of Making Same", to the same assignee.

BACKGROUND OF THE INVENTION

1. Field of the Invention

The present invention generally relates to medical devices and more particularly relates to male urinary catheters.

2. Description of the Prior Art

It has been known for some time to utilize a male urinary catheter for patients who are hospitalized or otherwise confined to bed. Oftentimes such catheters are also used for patients suffering from temporary or chronic incontinence. The earliest devices were simply tubes inserted into the urethra. However, this technique is particularly susceptible to causing infection. Discomfort and pain are also characteristics of this approach.

A major improvement in this field is the use of a condom catheter. This is a device having a sheath which is placed over the penis of the patient. A catheter stem is sealingly coupled to the distal end of the sheath. With this approach, the patient experiences much less opportunity for infection of the urinary track. However, there has been great difficulty with sealing the sheath against the penis to prevent unwanted fluid egress. The earliest attempts to seal the system applied constrictive pressure using an elastic band or tape.

A very significant technique for sealing a male condom catheter is taught by Conway et al, in U.S. Pat. No. Re. 33,206. This reference uses a layer of adhesive which is sandwiched between a layer of silicone rubber and a layer of latex rubber. In accordance with the preferred embodiment of Conway et al, the layer of latex rubber comprises the sheath of the condom catheter and the layer of silicone rubber is used as a release layer. The entire structure is rolled up from its proximal end prior to use. As the sheath is unrolled, the adhesive is released from the outer silicone rubber layer and adheres more tightly to the inner latex rubber layer. The unrolled sheath, having adhesive attached to its inner surface, readily adheres to the penis as well creating the desired leak-free bond.

Though the device of Conway et al, represents a substantial improvement over the prior art techniques, it is often desirable to fabricate the sheath from silicone rubber rather than latex rubber. Such a change in materials may be preferred according to the biocompatible properties of the silicone rubber. However, it tends to be difficult to obtain adhesion with a silicone rubber sheath. It is further desirable to obviate the need for the separate release layer.

SUMMARY OF THE INVENTION

The present invention overcomes the disadvantages found in the prior art by providing a male condom catheter employing a sheath of silicone rubber. The resulting structure is readily manufacturable and easy to use. It provides a leak-proof seal between the silicone rubber sheath and the penis of the patient.

The sheath is developed by dipping a mandrel form into silicone rubber and properly precuring it. The thickness may be increased by successive dipping and precuring operations. To assist in establishing consistent sheath thickness, a slightly textured form mandrel may be used. A release coating may be applied to the form mandrel before the first dipping step to aid in removing the finished product.

The adhesive layer is added to the outside surface of the sheath. The adhesive is cured.

A surface preparation layer is added to the adhesive layer over the adhesive area and permitted to devolatize. The completed structure is rolled up and removed from the form mandrel. The system is applied by unrolling onto the penis of the patient. The adhesive layer is readily removed from the outer surface of the sheath but easily adheres to the inner surface because of the intervening layer of surface preparation. The adhesive readily adheres to the skin of the patient.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
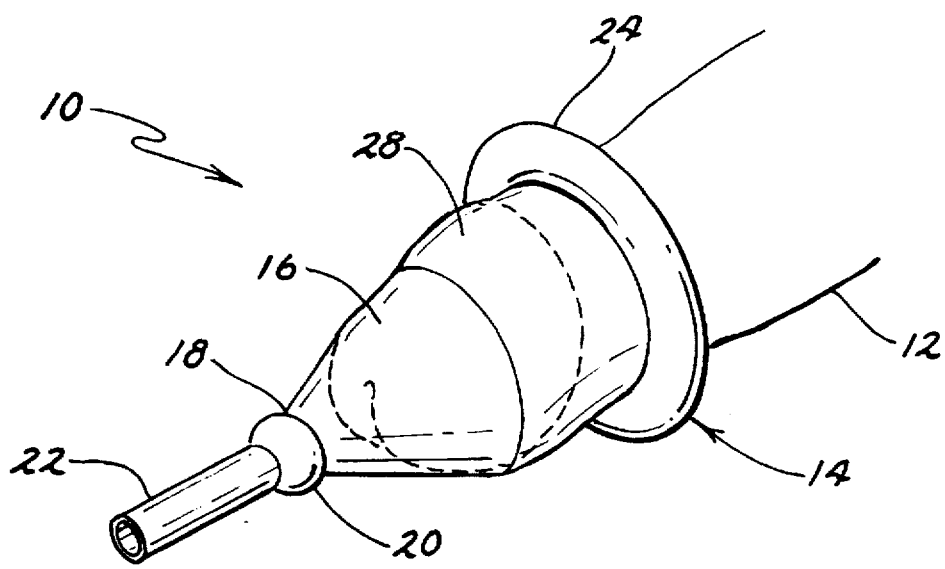
FIG. 1 is a perspective view of a male condom catheter according to the present invention as applied to the penis of a patient.

FIG. 1 is a perspective view of male condom catheter 10 during the process of being applied to penis 12 of the patient. Sheath 28 of male condom catheter 10 in the rolled up state 14 is placed at the distal end of penis 12. Sheath 28 is unrolled from distal to proximal end of penis 12. Distal to sheath 28 is sealingly attached conical reducer 16 which reduces to minimal diameter 18. Surge chamber 20 empties into catheter stem 22 which is coupled to the urine collection system (not shown).

Sheath 28 is preferably an expandable tube of silicone rubber. It should be sufficiently elastic to readily stretch over the normally flaccid penis of the patient without undue constriction of the blood flow. Conical reducer 16 and catheter stem 22 may have substantially greater wall thickness as they are not intended to stretch appreciably. Surge chamber 20 is intended to accommodate instantaneous changes in fluid volume. As sheath 28 is unrolled, adhesive layer 24 disengages the outer surface, adhering instead to the preparation layer on the inner surface of sheath 28 as discussed in more detail below.

Figure 2:
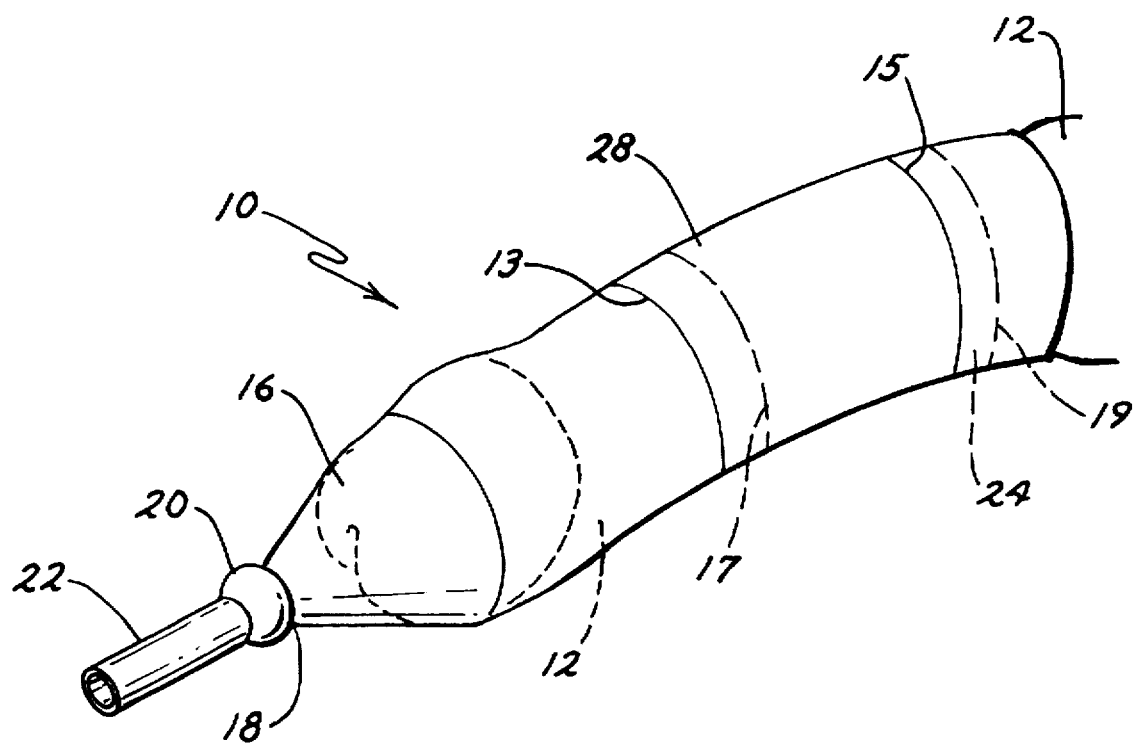
FIG. 2 is a perspective view of the device as completely applied.

FIG. 2 is a perspective view of male condom catheter 10 following the complete unrolling of sheath 28. Because the adhesive layer 24 adheres much more strongly to the preparation layer (not shown in this Figure) than to the silicone rubber sheath 28 directly, adhesive layer 24 is removed from the outer surface of sheath 28 and deposited on the inner surface. During manufacture, adhesive layer 24 (along with preparation layer 26) is applied to the area between lines 13 and 15 on the outer surface of sheath 28. The rolling and unrolling of sheath 28 moves adhesive layer 24 to the area between phantom lines 17 and 19 on the inner surface. All other referenced elements are as previously discussed.

Figure 3:
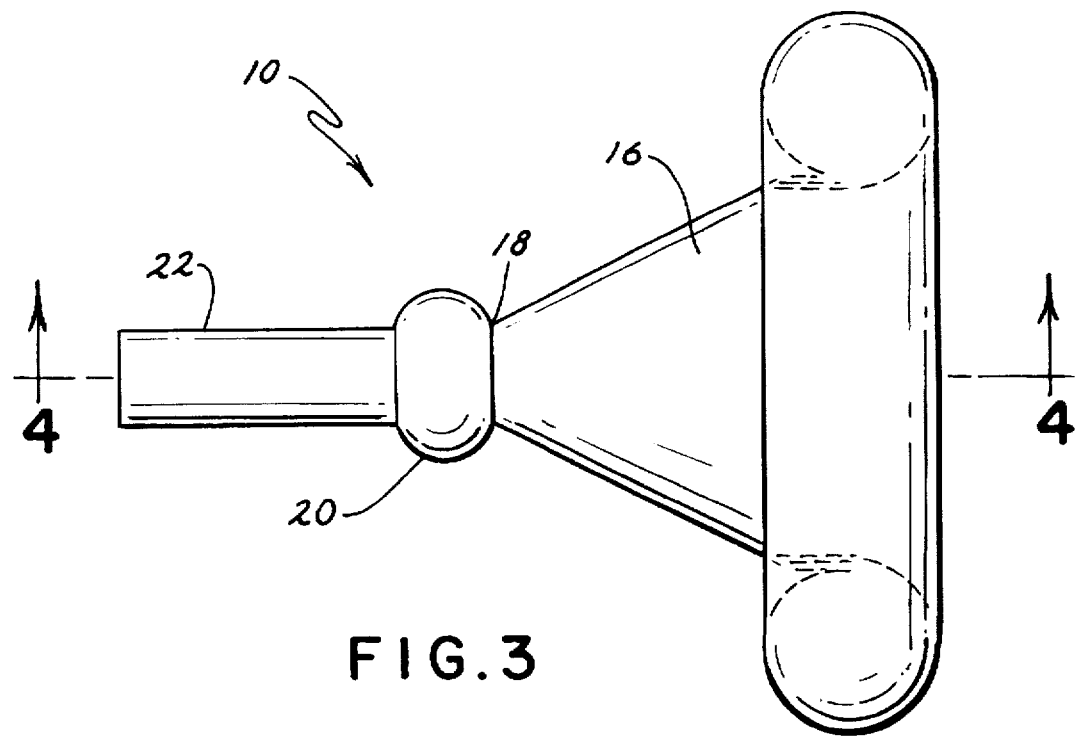
FIG. 3 is a schematic view of a catheter of the present invention as rolled up prior to use.

FIG. 3 is a close up view of male condom catheter 10 as supplied by the manufacturer but before installation on the patient. All referenced elements are as previously described.

Figure 4:
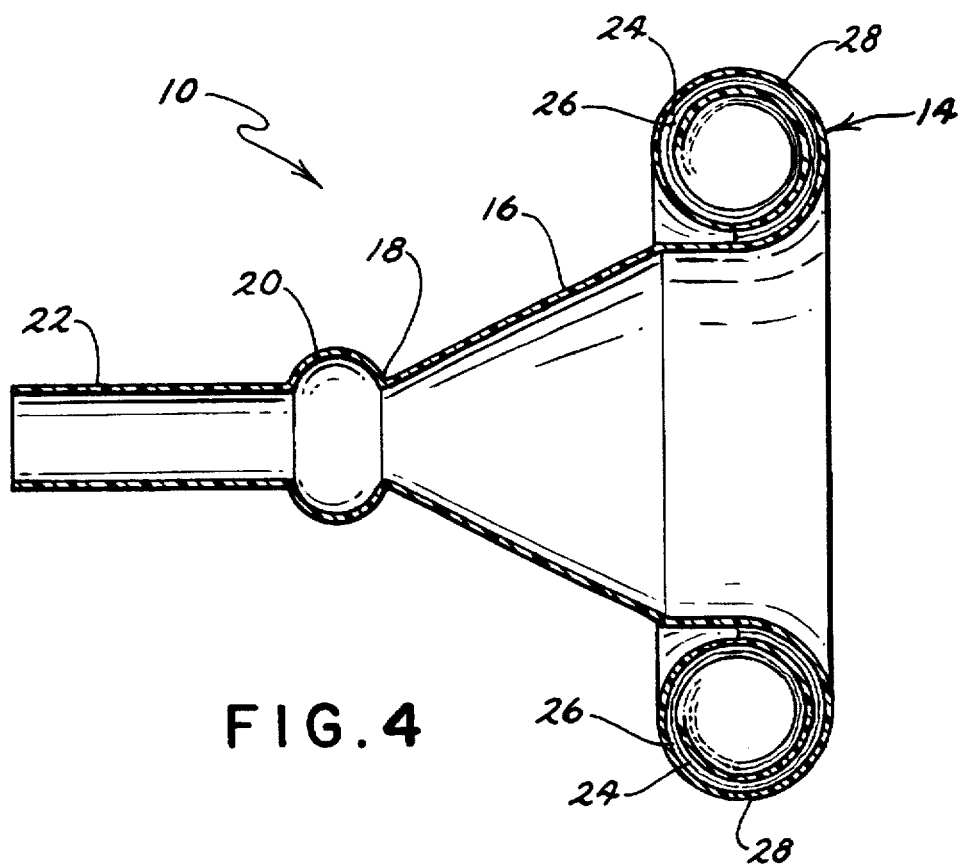
FIG. 4 is a sectioned view of the catheter of FIG. 4.

FIG. 4 is a schematic view showing the movement of adhesive layer 24 from the outside surface of sheath 28 to its inside surface as a result of the action of preparation layer 26 during rolling and unrolling of sheath 28 from the proximal end. All referenced elements are as previously described.

Figure 5:
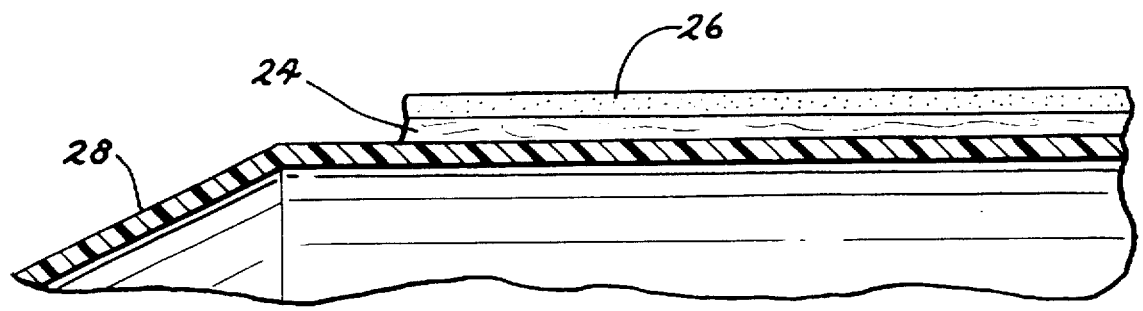
FIG. 5 is a schematic view of the various layers prior to being rolled up.

FIG. 5 is a schematic view of the three principle layers of male condom catheter 10 prior to being rolled up initially. Sheath 28 is fabricated from silicone rubber by dipping a form mandrel and precuring the material. Adhesive layer 24 is a standard medical grade adhesive which is applied on the outer surface of sheath 28. In this state, adhesive layer 24 only mildly adheres to sheath 28. Preparation layer 26 is formed of one of the known materials which prepares the inner surface of silicone rubber sheath 28 for adhesion to the adhesive layer 24.

During the manufacturing process, care must be exercised to properly register adhesive layer 24 and preparation layer 26. If preparation layer 26 is permitted to contact the outer surface of sheath 28, it will tend to adhere to the extent that it is difficult to unroll male condom catheter 10 when applying to the patient. If adhesive layer 24 is permitted to overlap preparation layer 26, it will directly contact a portion of the inner surface of sheath 28 after being rolled up and will not properly adhere without benefit of surface preparation.

Figure 6:
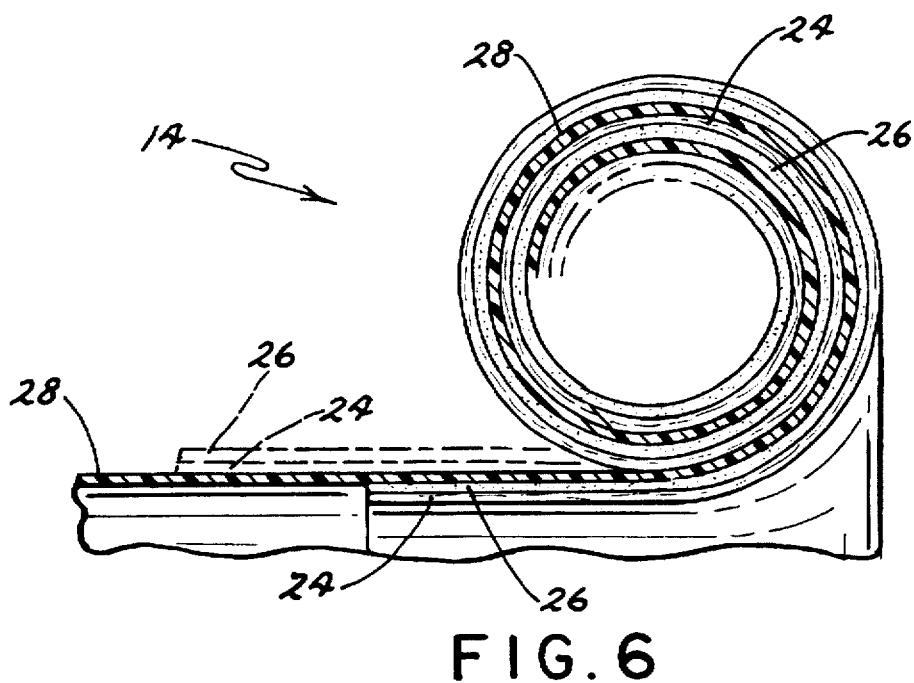
FIG. 6 is a close up section view showing a relative positioning of the various layers as rolled up.

FIG. 6 is a sectioned schematic view of sheath 28 after having been rolled up and in the process of being unrolled. Note that because preparation layer 26 contacts the inner surface of sheath 28 directly, adhesive layer 24 is caused to adhere to the prepared inner surface of sheath 28. This results in removing adhesive layer 24 from the outer surface of sheath 28 and depositing it on the inner surface. All other referenced elements are as previously described.

Figure 7:
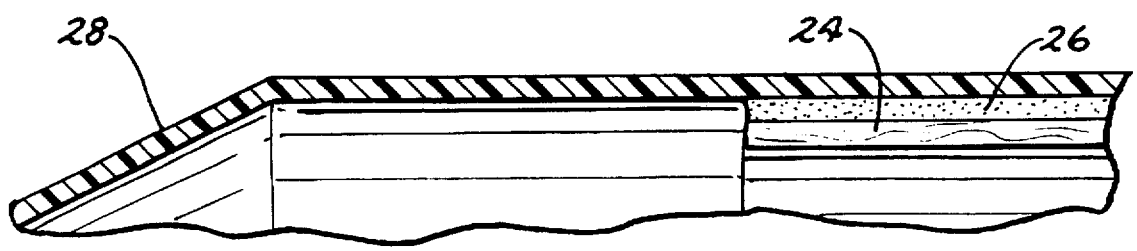
FIG. 7 is a schematic view of the various layers after installation.

FIG. 7 is a schematic view of the three principle layers of male condom catheter 10 after installation on the penis of a patient (not shown). Notice that because of the effect of preparation layer 26, adhesive layer 24 has been completely removed from the outside surface of sheath 28 and deposited on its inner surface. As explained above, adhesive layer 24 readily adheres to the skin of the patient.

Figure 8:
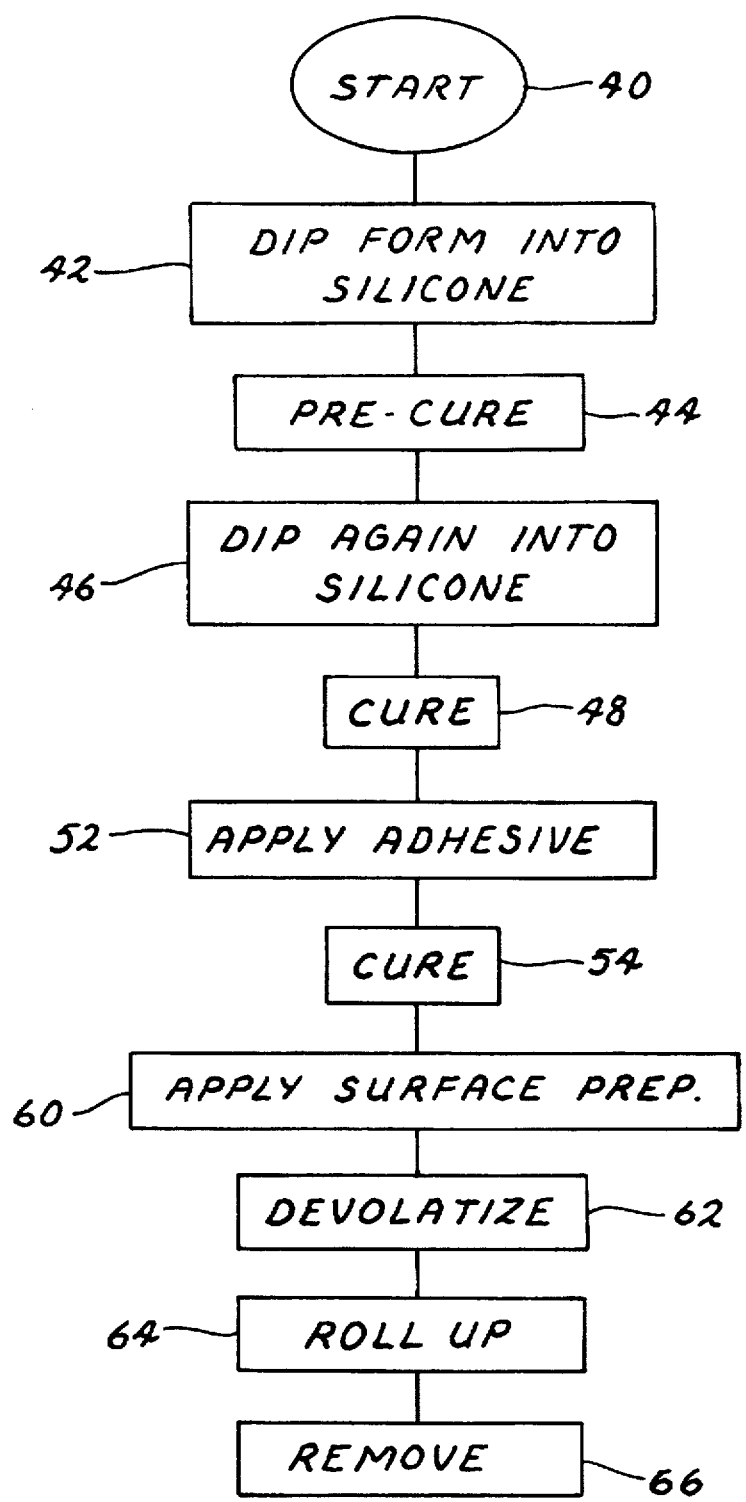
FIG. 8 is a flowchart showing the various key steps of the manufacturing process.

FIG. 8 is a simplified flow chart 38 showing the key steps of the manufacturing process of male condom catheter 10. The process begins at element 40 with the selection and solvent cleaning of a form mandrel. Alcohol is a typical solvent for this purpose. The mandrel is formed in the shape normally used for fabrication of a condom. The form mandrel may be lightly textured to permit consistency in the dipping step. Also the textured form mandrel may be pre-dipped or otherwise coated with a release agent to permit ease in disengaging the completed assembly.

The form mandrel is dipped into the silicone rubber at element 42 for a period consistent with the manufacturer's specifications, typically 3 to 5 minutes. The material is precured at element 44 as per the supplier's recommendation, usually about 50 degrees centigrade for 15 minutes. To obtain the desired thickness, elements 46 and 48 repeat elements 42 and 44.

Application of the adhesive layer 24 and the preparation layer 26 is in strict accordance with the need for proper registration as explained above. The adhesive layer 24 is applied to the outer surface of sheath 28 by brushing or spraying at element 52 and curing at element 54. The preparation layer 26 is similarly applied at element 60 and devolatized at element 62. The structure is rolled up for packaging at element 64 and removed from the form mandrel at element 66. The completed system is packaged in accordance with standard regulatory requirements.

Having thus described the preferred embodiments of the present invention, those of skill in the art will be readily able to make and use yet other embodiments within the scope of the claims hereto attached.

We claim:

1. A method of manufacturing an external male catheter, said external male catheter having an exterior surface, an interior surface, a distal end, and a proximal end, said method comprising the steps of:

dipping a form mandrel into silicone rubber to produce a substrate defining the interior surface and the exterior surface of the external male catheter;

precuring said substrate;

applying an adhesive layer to a predetermined region of the exterior surface of the substrate;

curing at least the adhesive layer or the substrate;

applying a surface preparation material overlying the adhesive layer, said surface preparation material having an affinity for the silicon rubber which is greater than that of the adhesive layer; and rolling the substrate upon itself from the proximal end toward the distal end to a rolled configuration such that a portion of the interior surface lies in close confronting relation to a distinct region of the interior surface, the surface preparation material contacting the distinct region of the interior surface of the substrate with the adhesive layer being transferred directly to the interior surface from the exterior surface.

2. The method of claim 1 wherein the external male catheter is unrolled from the rolled configuration, and further wherein the adhesive layer transfers from the exterior surface to the interior surface of the external male catheter when the external male catheter is rolled and subsequently unrolled.

3. The method of claim 1 wherein the surface preparation material is initially volatile when applied to the adhesive layer, and wherein the method further comprises the step of:

devolatizing the surface preparation material after the surface preparation material is applied to the adhesive layer and before the substrate is rolled upon itself.

4. The method of claim 1 wherein the predetermined region on the exterior surface of the external male catheter to which the adhesive layer is applied is disposed more closely proximate to the distal end of the external male catheter than the distinct region on the interior surface of the external male catheter to which the adhesive layer is transferred when the external male catheter is rolled and unrolled.

5. A method for manufacturing an external male catheter, said external male catheter having an exterior surface, an interior surface, a distal end, and a proximal end, said method comprising the steps of:

providing a substrate defining the interior surface and the exterior surface of the external male catheter;

applying an adhesive layer to a predetermined region of the exterior surface of the substrate;

applying a surface preparation material overlying the adhesive layer, said surface preparation material having an affinity for the substrate which is greater than that of the adhesive layer; and rolling the substrate upon itself from the proximal end toward the distal end to a rolled configuration such that a portion of the interior surface lies in close confronting relation to a distinct region of the interior surface, the surface preparation material contacting said distinct region of the interior surface with the adhesive layer being transferred directly to said distinct region of the interior surface.

6. The method of claim 5 wherein the substrate is fabricated substantially from a silicone rubber.

* * * * *